United States Patent
Berg et al.

(10) Patent No.: US 7,264,936 B2
(45) Date of Patent: Sep. 4, 2007

(54) METHOD FOR DETECTING PROCOAGULANT GENETIC AND METABOLIC CONDITIONS ASSOCIATED WITH, AND POTENTIALLY PREDISPOSITIONAL FOR, ACTIVATION OF THE COAGULATION RESPONSE

(76) Inventors: David E. Berg, 1101 E. Waltann, Phoenix, AZ (US) 85022; Lois Hill Berg, 1101 E. Waltann, Phoenix, AZ (US) 85022; Harold H. Harrison, 11701 N. 99th St., Scottsdale, AZ (US) 85260

( * ) Notice: Subject to any disclaimer, the term of this patent is extended or adjusted under 35 U.S.C. 154(b) by 63 days.

(21) Appl. No.: 10/915,018

(22) Filed: Aug. 10, 2004

(65) Prior Publication Data

US 2005/0069969 A1 Mar. 31, 2005

Related U.S. Application Data

(63) Continuation of application No. 09/966,311, filed on Sep. 28, 2001, now abandoned, which is a continuation of application No. 09/637,808, filed on Aug. 11, 2000, now Pat. No. 6,692,969.

(60) Provisional application No. 60/148,799, filed on Aug. 13, 1999.

(51) Int. Cl.
*G01N 33/53* (2006.01)

(52) U.S. Cl. ...................................... 435/7.1
(58) Field of Classification Search ................ 435/7.1
See application file for complete search history.

(56) References Cited

U.S. PATENT DOCUMENTS

| 5,780,255 A * | 7/1998 | Preda .......................... 435/23 |
| 2006/0068454 A1 * | 3/2006 | Okuda et al. ................. 435/13 |

OTHER PUBLICATIONS

Sorensen et al (Thrombosis Research vol. 65, pp. 479-486, 1992).*
Pedersen et al (Heart vol. 77, pp. 122-127, 1997).*

* cited by examiner

*Primary Examiner*—Mark Navarro
(74) *Attorney, Agent, or Firm*—Parsons & Goltry; Michael W. Goltry; Robert A. Parsons

(57) ABSTRACT

Methods for diagnosing and identifying genetic and metabolic factors associated with a physiologic procoagulant predisposition for and concurrent activation of the coagulation response in patients suffering from conditions such as chronic fatigue syndrome, fibromyalgia, Gulf War illness and cardiovascular disease are disclosed. Diagnostic assays utilized in the methods include measurement of blood levels of Protein C, Protein S, antithrombin, activated protein C resistance, prothrombin, plasminogen activator inhibitor-1, lipoprotein (a) and homocysteine. Treatment regimens include anticoagulant therapies comprising administering warfarin or heparin as needed.

1 Claim, No Drawings

METHOD FOR DETECTING PROCOAGULANT GENETIC AND METABOLIC CONDITIONS ASSOCIATED WITH, AND POTENTIALLY PREDISPOSITIONAL FOR, ACTIVATION OF THE COAGULATION RESPONSE

RELATED APPLICATIONS

This application claims the benefit of pending U.S. Non-Provisional Patent Application Serial. No. 09/966,311, filed on 28 Sep. 2001 now abandoned, which claims the benefit of U.S. Non-Provisional Patent Application Serial No. 09/637,808, filed 11 Aug. 2000 now U.S. Pat. No. 6,692,969, which in turn claims the benefit of U.S. Provisional Patent Application Ser. No. 60/148,799, filed 13 Aug. 1999.

This invention relates to methods for diagnosing and identifying genetic and metabolic procoagulant factors associated with predisposition for and/or concurrent activation of the coagulation response which may respond to anti-coagulant therapy. For the purpose of this filing the term procoagulant factor refers to an abnormal result in the group of tests which presently includes: Protein C, Protein S, antithrombin, activated protein C resistance, prothrombin, plasminogen activator inhibitor-1, lipoprotein (a) and homocysteine.

BACKGROUND OF THE INVENTION

Chronic fatigue syndrome (CFS), fibromyalgia (FM), Gulf War Illness (GWI) and related chronic illnesses have been considered diagnoses of exclusion where no other diagnosis fits well. CFS has been defined by specific requirements of fatigue, its duration, associated symptoms, and initial clinical and laboratory evaluation. There has existed no reliable laboratory means for determining whether an individual was suffering from CFS, FM, or some other disease. Gulf War illness and CFS share many clinical characteristics and may be variations of similar underlying pathophysiology. Accordingly, a felt need for a method of testing for CFS, FM, and related illnesses, such as GWI, existed. We have previously demonstrated low level activation of coagulation in many of these patients by measurement of blood levels of fibrinogen, prothrombin fragment 1+2, thrombin-antithrombin complexes, soluble fibrin monomer, and platelet CD62P activation. We have now conducted analyses of underlying genetic and metabolic factors that could contribute to a predisposition to develop such illnesses or yield a more enhanced activation of coagulation in patients who acquire the illnesses. These new tests include Protein C, Protein S, antithrombin, activated protein C resistance, prothrombin activity, plasminogen activator inhibitor-1, lipoprotein (a) and homocysteine. Various methods including protein, enzymatic activity, amino acid analysis and analysis of gene sequences apply to these genetic and metabolic procoagulant markers.

SUMMARY OF THE INVENTION

The current invention relates to a method for diagnosing and identifying genetic and metabolic procoagulant factors that are 1) associated with hereditary predisposition for activation of the coagulation response, or 2) occur in patients who have measurable minimal activation of the coagulation response; and whose initial clinical evaluation indicates chronic fatigue syndrome, fibromyalgia, Gulf War illness and related conditions; and whose low level activation of coagulation can be treated using anticoagulant therapies. The present invention further identifies underlying procoagulant factors that may 1) guide treatment of the condition using anticoagulant therapies; 2) be used to identify asymptomatic family members and close contacts who may be at risk for such disorders and, once identified, may be monitored and treated more effectively given the knowledge of the underlying hereditary genetic and metabolic procoagulant condition.

We have previously discovered that we may reliably diagnose a patient suffering from CFS, FM or GWI by evaluating the status of the coagulation response in that patient by using a novel combination of tests which can detect minimal activation of the coagulation response. This novel combination includes tests for determining levels of fibrinogen, prothrombin fragment 1+2, thrombin/antithrombin complexes, soluble fibrin monomer, and platelet activation by flow cytometry. These assays are highly sensitive to minimal deviation from normal. Deviation from the normal values in any two of the five assays permits diagnosis of CFS, FM, GWI or other disease associated with activation of the coagulation response. Once a condition associated with activation of the coagulation response has been diagnosed, the patient is treated with anticoagulant therapy, such as heparin followed by warfarin or warfarin alone. Coumarins or coumarin derivatives may also be used. Heparin can be defined as heparin (porcine or bovine) or any of its derivatives, such as low molecular weight heparin (LMWH), oral heparin, heparinoids, or any other designer heparin-like drugs. It is presently preferred that a low dose anticoagulant therapy be used. Patient progression and recovery is then monitored using the novel combination of assays. We have observed that a majority of individuals diagnosed as CFS and/or FM on clinical criteria may be defined as having an antiphospholipid antibody syndrome (APS) that is induced or generated by pathogens that invade endothelial cells and induce antibodies that can trigger the low level activation of coagulation that we detect. In addition, patients with immune-mediated chronic inflammatory disorders of many types can have low level activation of the coagulation response. Therefore, patients with a spectrum of chronic inflammatory processes may have low level activation of coagulation as part of their pathophysiology. We postulate that our tests for activation of the coagulation and platelet systems also have application to other conditions which stem from activation of the coagulation response. This has been validated by preliminary studies of patients suffering with multiple sclerosis, breast implant sickness syndrome, fetal wastage syndrome, gulf war illness, inflammatory bowel disease, autism. As with CFS and FM, once diagnosed using our combination of assays, these patients may be treated with anticoagulant therapies, and their treatment and recovery monitored using our combination of tests.

We postulate that our combination of tests for detecting minimal activation of coagulation response also has application to detecting and treating, Sjogrens syndrome, late Lyme disease (also called chronic Lyme disease), transient ischemic attack, attention deficit disorder, Alzheimer's disease, Parkinson's disease, as well as some cardiovascular diseases. Once diagnosed using our combination of ISAC assays, these patients should also benefit from treatment with anticoagulant therapies, and their treatment and recovery monitored using our combination of tests. We postulate that the present group of assays for procoagulant genetic and metabolic factors may also be used in patients with these other conditions to help determine and guide anticoagulant and ancillary therapies.

The Presently Preferred Assays Used to Determine a Propensity for a Procoagulant Clinical State The abnormalities of genes and their gene products that are currently known to represent hereditary and acquired procoagulant genetic and metabolic factors are those that cause: decreased Protein C activity, decreased Protein S activity, decreased antithrombin (formerly known as antithrombin III) levels, activated protein C resistance (Factor V Leiden and other mutations yielding factor Va that is resistant to inactivation by activated protein C), increased prothrombin levels, increased plasminogen activator inhibitor-1 levels, increased Lp(a) levels, and increased homocysteine levels. Our current assays are designed to detect the types of abnormalities cited above and use analysis of gene sequences, mass or enzyme assays of polypeptide gene products, or the metabolic products of gene action.

DETAILED DESCRIPTION OF THE INVENTION

For the purposes of describing the invention, we discuss the form of the method of the present invention which is presently preferred; it being understood, however, that this invention is not limited to the precise arrangements, instrumentalities, and assays discussed.

Furthermore, the number of procoagulant hereditary genetic and metabolic factors in the present method is subject to future change.

Our novel method for diagnosing genetic and metabolic factors that occur in, and that may be predispositional to, CFS, FM, and related conditions uses a novel combination of assays related to a proposed hereditary propensity for minimal activation of the coagulation response. Our new method extends our studies of CFS, FM, GWI and related chronic illness patients to genetic and metabolic factors which are procoagulant by virtue of establishing a propensity for hypercoagulability due to either a thrombophilic state (Protein C, Protein S, antithrombin, activated protein C resistance, and prothrombin activity) or a hypofibrinolytic state (plasminogen activator inhibitor-1, lipoprotein (a) and homocysteine). Patient progression and recovery on anticoagulant therapy is then monitored using the novel Immune System Activation of Coagulation (ISAC) combination of assays. However, we postulate that results of the procoagulant genetic and metabolic assays can be used to guide treatment and therapeutic modality choices.

In a study with CFS/FM patients, twenty-five of 30(83%) had a hereditary abnormality (Table I). This is approximately a 4 times higher rate of occurrence of a procoagulant state in the patients than in the controls and that would be found in random population screening for the same factors. Statistical analysis shows this to a be a statistically significant clinical association which supports the hypotheses we have proposed. In order to further test our method, we conducted a blinded study of 33 GWI patients and 33 controls, for a total of 66 individuals (Tables II & III). According to our method, blood drawn from all individuals was subjected to each of the 5 ISAC tests and the eight genetic and metabolic factors panel. Using our presently preferred combination of 5 assays, we determined that the GWI patients could be reliably distinguished from the controls. Of the 33 patients, 20 (61%) had positive hereditary defects: eight of 33 were positive for thrombophilia, seven were positive for hypofibrinolysis, and five had a risk factor in each group.

The following tables set out the results for each group tested.

TABLE I

PROCOAGULANT GENETIC & METABOLIC POSITIVITY IN CFS/FM

| Patients | No. | AT | PC | PS | II | Lp(a) | PAI-1 | HC | 1 Abn | >1 Abn |
|---|---|---|---|---|---|---|---|---|---|---|
| M | 5 | 0 | 0 | 0 | 1 | 2 | 2 | 2 | 4 | 2 |
| F | 25 | 0 | 0 | 3 | 8 | 9 | 9 | 8 | 21 | 14 |
| Total (n) | 30 | 0 | 0 | 3 | 9 | 11 | 11 | 10 | 25 | 16 |
| % | | 0 | 0 | 10 | 30 | 37 | 37 | 33 | 83 | 53 |

TABLE II

CONTROL VS PATIENT GROUP ISAC TEST RESULTS IN GWI:

| | TEST: | | | | | | |
|---|---|---|---|---|---|---|---|
| | 62P | +ADP | PA Index | FIB | SFM | TAT | F1 + 2 |
| Ref Range | 0-27 | 40-80 | Normal | 180-310 | 0-17 | 1.0-4.1 | 0-1.1 |
| Control Mean | 18 | 53 | 0% Pos | 276 | 11 | 1.7 | 1.0 |
| Patient Mean | 33 | 38 | 54% Pos | 301 | 19 | 2.5 | 1.3 |

TABLE III

PROCOAGULANT GENETIC & METABOLIC POSITIVITY IN GWI

| | ISAC Tests Positive: | | | |
|---|---|---|---|---|
| | 1/5 Tests | 2/5 Tests | 3/5 Tests | 4/5 Tests |
| Inc PC, PS, &/or AT | 6/10 | 5/10 | 6/11 | 0/1 |
| Positive Procoagulant & Genetic Risk Factors | 8/10 | 5/10 | 5/11 | 1/1 |

Defects in each of the factors described contribute to procoagulant modulation of the coagulation cascade—either through promotion of fibrin or clot formation (thrombophilia) or inhibition of clot breakdown and fibrin clearance (hypofibrinolysis).

The activation of coagulation results in generation of thrombin. Thrombin then acts on fibrinogen to generate fibrin. At high levels of activation, clot formation is triggered while at low levels of activation only soluble fibrin is generated. We have proposed a model of CFS, FM, GWI, and related disorder pathophysiology in which the soluble fibrin monomer generated by low level activation of coagulation is deposited at the endothelial surface of the microvasculature with consequent diminution in oxygen and nutrient transfer across such endothelial boundaries.

Antithrombin combines with thrombin to form thrombin/antithrombin complexes, which are then removed from the blood.

Antithrombin is a slow inhibitor of thrombin, but in the presence of heparin, antithrombin reacts with thrombin at a greatly increased rate. Activated protein C/antitrypsin complex is a secondary inhibitor of thrombin generation.

When more thrombin is generated than can be removed by the thrombin inhibitors, thrombin reacts with fibrinogen to create an intermediate protein called soluble fibrin monomer. Soluble fibrin monomer is a sticky protein which increases blood viscosity and forms deposits on capillary wall endothelial cells. The soluble fibrin monomer which is deposited on the capillary walls, a phenomenon called fibrin deposition, may block the passage of nutrients through the capillary walls to the surrounding tissues, whether it is another capillary, muscle or organ tissue. We have postulated that the increase in blood viscosity in combination with associated blockage in nutrient transfer results in the fatigue of CFS, the muscle pain of FM, and contributes to the pathology of other chronic inflammatory illnesses. This could also be part of the explanation (pathology) of fetal demise and spontaneous abortions seen in recurrent miscarriages (fetal wastage syndrome).

Patients with immune mediated chronic inflammatory disorders of many types can have low level activation of the coagulation response. Therefore, patients with a spectrum of chronic inflammatory processes may have low level activation of coagulation as part of their pathophysiology. We postulate that our tests for activation of the coagulation and platelet systems also have application to other conditions which stem from activation of the coagulation response. This has been validated by preliminary studies of patients suffering with multiple sclerosis, breast implant sickness syndrome, gulf war illness, inflammatory bowel disease, autism, and fetal wastage syndrome. As with CFS and FM, once diagnosed using our combination of assays, these patients may be treated with anticoagulant therapies, and their treatment and recovery monitored using our combination of tests. We propose that a common feature of these conditions is the chronic inflammatory process that stimulates low level activation of coagulation. We further propose that there is a fundamental procoagulant propensity in the majority of these patients that either predisposes to development of the chronic clinical condition or aids in its maintenance by tipping the coagulation system balance towards hypercoagulability.

We postulate that our combination of tests for detecting genetic and metabolic factors of procoagulant propensity in disorders with minimal activation of the coagulation response also has application to detecting and treating other immune mediated chronic inflammatory disorders such as Sjogrens syndrome, late Lyme disease (also called chronic Lyme disease), transient ischemic attack, attention deficit disorder, Alzheimer's disease, Parkinson's disease, as well as some cardiovascular diseases. Once diagnosed using our combination of assays, these patients should also benefit from treatment with anticoagulant therapies, and their treatment and recovery monitored using our combination of tests.

We claim:

1. A method for determining whether a blood sample has a hereditary propensity for hypercoagulability comprising steps of:
   identifying a group of genetic and metabolic procoagulant factors that each when defective contribute to procoagulant modulation of a coagulation cascade in blood;
   the genetic and metabolic procoagulant factors comprising a Protein C factor, a Protein S factor, an antithrombin factor, an activated protein C resistance factor, a prothrombin factor, a plasminogen activator inhibitor-1 factor, a lipoprotein (a) factor, and a homocysteine factor; wherein
       a defect in the Protein C factor comprises a decreased Protein C activity;
       a defect in the Protein S factor comprises a decreased Protein S activity;
       a defect the antithrombin factor comprising decreased antithrombin levels,
       a defect in the activated protein C resistance factor comprising an activated protein C resistance,
       a defect in the prothrombin factor comprising increased prothrombin levels,
       a defect in the plasminogen activator inhibitor-1 factor comprising increased plasminogen activator inhibitor-1 levels,
       a defect in the lipoprotein (a) factor comprising increased lipoprotein (a) levels, and
       a defect in the homocysteine factor comprising increased homocysteine levels;
   providing a blood sample;
   testing the blood sample to determine whether any of the genetic and metabolic procoagulant factors of the group of genetic and metabolic procoagulant factors is defective; and
   if at least one of the genetic and metabolic procoagulant factors of the group of genetic and metabolic procoagulant factors is defective, diagnosing the blood sample as having a hereditary propensity for hypercoagulability.

* * * * *